(12) United States Patent
Towe et al.

(10) Patent No.: US 11,141,596 B2
(45) Date of Patent: Oct. 12, 2021

(54) WIRELESS MULTICHANNEL NEUROSTIMULATORS AND METHODS FOR USING THE SAME

(71) Applicant: Arizona Board of Regents on behalf of Arizona State University, Scottsdale, AZ (US)

(72) Inventors: Bruce C. Towe, Mesa, AZ (US); Jitendran Muthuswamy, Chandler, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 143 days.

(21) Appl. No.: 16/274,309

(22) Filed: Feb. 13, 2019

(65) Prior Publication Data

US 2019/0247668 A1 Aug. 15, 2019

Related U.S. Application Data

(60) Provisional application No. 62/629,856, filed on Feb. 13, 2018.

(51) Int. Cl.
*A61N 1/36* (2006.01)
*A61N 1/372* (2006.01)
*A61N 1/05* (2006.01)

(52) U.S. Cl.
CPC ....... *A61N 1/37217* (2013.01); *A61N 1/0551* (2013.01); *A61N 1/36003* (2013.01); *A61N 1/36062* (2017.08); *A61N 1/36103* (2013.01)

(58) Field of Classification Search
CPC ............ A61N 1/37217; A61N 1/36062; A61N 1/0551; A61N 1/36003; A61N 1/36103
See application file for complete search history.

(56) References Cited

U.S. PATENT DOCUMENTS

| 4,773,401 A | 9/1988 | Citak |
| 4,935,345 A | 6/1990 | Guilbeau et al. |

(Continued)

FOREIGN PATENT DOCUMENTS

| WO | 2004016315 A1 | 2/2004 |
| WO | WO2004/105583 | 12/2004 |

(Continued)

OTHER PUBLICATIONS

EP Application 09812106.4, Supplementary European Search Report, dated Sep. 6, 2013.

(Continued)

*Primary Examiner* — Ankit D Tejani
*Assistant Examiner* — Joshua Brendon Solomon
(74) *Attorney, Agent, or Firm* — Lewis Roca Rothgerber Christie LLP (57) ABSTRACT

A micro-scale implantable bioelectronic medical device system that allows multichannel neurostimulation of peripheral nerve bundles so to affect a more localized and specific control over neuromodulation of body tissues and organs. Such systems can be used in medical therapeutic applications for the treatment of a wide variety of disorders of the human body and may be applied in the growing field of medical neuromodulation. Systems and processes may also provide a way of interfacing to nerve and muscle for purposes of the control of advanced robotic prosthetics as well as man-machine interfaces. Apparatus, systems and processes may be adapted in various embodiments to the stimulation of brain and other bioelectrically excitable tissues in the human body as well.

20 Claims, 6 Drawing Sheets

(56) References Cited

U.S. PATENT DOCUMENTS

| | | | |
|---|---|---|---|
| 7,702,395 B2 | 4/2010 | Towe et al. | |
| 8,282,561 B2 | 10/2012 | Towe | |
| 8,340,773 B2 | 12/2012 | Towe et al. | |
| 8,369,956 B2 | 2/2013 | Towe et al. | |
| 8,626,303 B2 | 1/2014 | Towe et al. | |
| 8,725,270 B2 | 5/2014 | Towe | |
| 8,774,928 B2 | 7/2014 | Towe et al. | |
| 8,909,343 B2 | 12/2014 | Towe | |
| 9,446,255 B2 | 9/2016 | Towe et al. | |
| 9,457,196 B2 | 10/2016 | Towe et al. | |
| 9,555,258 B2 | 1/2017 | Towe et al. | |
| 9,693,708 B2 | 7/2017 | Towe | |
| 9,700,712 B2 | 7/2017 | Towe | |
| 10,016,612 B2 | 7/2018 | Towe et al. | |
| 10,022,566 B2 | 7/2018 | Towe | |
| 10,252,085 B2 | 4/2019 | Towe et al. | |
| 10,441,803 B2 | 10/2019 | Towe et al. | |
| 10,463,856 B2 | 11/2019 | Towe | |
| 2008/0108915 A1 | 5/2008 | Penner | |
| 2011/0184495 A1* | 7/2011 | Wang | H05K 9/002 607/63 |
| 2012/0041310 A1 | 2/2012 | Towe | |
| 2012/0197342 A1 | 8/2012 | Towe | |
| 2013/0096435 A1 | 4/2013 | Towe | |
| 2013/0123882 A1 | 5/2013 | Towe | |
| 2013/0144361 A1 | 6/2013 | Towe | |
| 2013/0197609 A1* | 8/2013 | Moore | A61N 1/05 607/61 |
| 2015/0100110 A1* | 4/2015 | Towe | A61N 1/36125 607/61 |
| 2015/0148710 A1 | 5/2015 | Towe et al. | |
| 2015/0306429 A1 | 10/2015 | Towe et al. | |
| 2017/0095198 A1 | 4/2017 | Towe | |
| 2017/0258363 A1 | 9/2017 | Towe | |
| 2017/0274200 A1 | 9/2017 | Towe | |
| 2018/0093112 A1 | 4/2018 | Towe et al. | |
| 2019/0247668 A1 | 8/2019 | Towe et al. | |
| 2019/0282235 A1 | 9/2019 | Aramaki et al. | |
| 2019/0336777 A1 | 11/2019 | Towe et al. | |
| 2020/0061368 A1 | 2/2020 | Towe | |

FOREIGN PATENT DOCUMENTS

| | | |
|---|---|---|
| WO | 2008137703 A1 | 11/2008 |
| WO | 2010027963 A1 | 3/2010 |
| WO | 2010135634 A2 | 11/2010 |
| WO | 2011156495 A2 | 12/2011 |
| WO | 2012030962 A2 | 3/2012 |
| WO | 2013071290 A1 | 5/2013 |
| WO | 2013169363 A2 | 11/2013 |
| WO | 2013176744 A1 | 11/2013 |
| WO | 2014093332 A1 | 6/2014 |
| WO | 2015069446 A1 | 5/2015 |
| WO | 2015142842 A2 | 9/2015 |

OTHER PUBLICATIONS

W.B. Phillips et al, An Ultrasonically-Driven Piezoelectric Neural Stimulator, Harrington Department of Bioengineering, Arizona State University, Tempe, AZ, USA, pp. 1983-1986, Proceedings of the 25th Annual International Conference of the IEEE EMBS, Cancun, Mexico, Sep. 17-21, 2003.

Bruce C. Towe Member, IEEE, Passive Backscatter Biotelemetry for Neural Interfacing, pp. 144-147, Proceedings of the 3rd International IEEE EMBS Conference on Neural Engineering, Kohala Coast Hawaii, USA, May 2-5, 2007.

Ozeri, S. et al., "Ultrasonic transcutaneous energy transfer for powering implanted devices", Ultrasonics, May 2010 [available online Nov. 2009], vol. 50, No. 6, pp. 556-566 <DOI: 10.1016/j.ultras.2009.11.004>.

* cited by examiner

WIRELESS MULTICHANNEL NEUROSTIMULATORS AND METHODS FOR USING THE SAME

CROSS-REFERENCE TO RELATED APPLICATION

This application claims priority to U.S. provisional application 62/629,856, which was filed on Feb. 13, 2018 and is entitled Wireless Multichannel Neurostimulators and Methods for Using the Same. The '856 application is incorporated in its entirety by reference into this application.

GOVERNMENT RIGHTS

This invention was made with government support under HR0011-16-2-0023 awarded by DARPA, the government has certain rights in the invention.

TECHNICAL FIELD

Affirmative and receptive neurostimulation are referenced and described. More particularly, methods, devices, systems, and articles of manufacture related to multichannel affirmative and/or receptive neurostimulation using implantable micro-devices are provided.

BACKGROUND

Neurostimulation is considered a bioelectrical technique used in therapeutic relief of chronic pain, restoration of lost body function, treating damaged muscle and nerve function, and improving quality of life of amputees by activating a part of the nervous system. Existing neurostimulation technologies are related to pacemakers and use silicone electrode leads routed inside the body from an implantable battery pack and electric pulse generator. These electrode leads typically activate a specific nerve such as the vagus nerve or other major nerve trunk in the body.

Peripheral nerves leading to limbs and body organs contain hundreds to thousands of individual nerve fibers controlling different body functions. Neurostimulation of a whole nerve trunk, as often done in therapeutics, inevitably affects many body functions at one time. Some of these effects may be desired, and some may not. A major problem in the use of neural stimulation is achieving neural interfaces that allow a more exacting control over nerve function rather than a gross stimulation of an entire nerve trunk.

BRIEF SUMMARY

Affirmative and receptive neurostimulation may be provided or used in embodiments. This neurostimulation may comprise methods, devices, systems, and articles of manufacture related to multichannel affirmative and/or receptive neurostimulation using implantable micro-devices. These micro-devices may be implanted in various patients, including humans, and may serve to send or receive neurostimulation signals to or from one or more target areas of a patient. The level of granularity of the neurostimulation signals may provide for succinct or specific nerve fiber control or nerve fiber feedback. This specific nerve fiber control or nerve feedback may be employed in various operations and apparatus, which can include control or monitoring of prosthetics, control or monitoring of implants, and treatment of diseased tissue or other target areas of one or more patients. Proportional control as well as bipolar control and monitoring may also be provided in embodiments. In other words, embodiments may comprise methods, devices, systems, and articles of manufacture related to multichannel affirmative and/or receptive neurostimulation using implantable micro-devices where the affirmative and/or receptive neurostimulation may be performed or received on a proportional basis, i.e., in a range, or as a bipolar signal, e.g., high-low signal, i.e., having on and off, or yes and no—like a binary digital signal. Noise cancellation and smoothing techniques may be employed in embodiments such that either or both proportional and binary neurostimulations may be employed. Thus, when a range of responses are received, or signal noise is introduced when instructions are being sent, these noise-cancelling and/or smoothing techniques may be employed to improve results.

Embodiments may include one or more micro-scale implantable bioelectronic medical devices which, alone or in a grouping, may allow multichannel neurostimulation of peripheral nerve bundles so to affect a more localized and specific control over neuromodulation of body tissues and organs. Embodiments may also provide for medical therapeutic applications in the treatment of a wide variety of disorders of the human body, which may benefit from neuromodulation. Embodiments may also be employed when interfacing with nerve and muscle for purposes of control of advanced robotic prosthetics as well as man-machine interfaces. Similarly, embodiments may also be adapted in the stimulation of brain and other bioelectrically excitable tissues of the human body.

Figure 4:
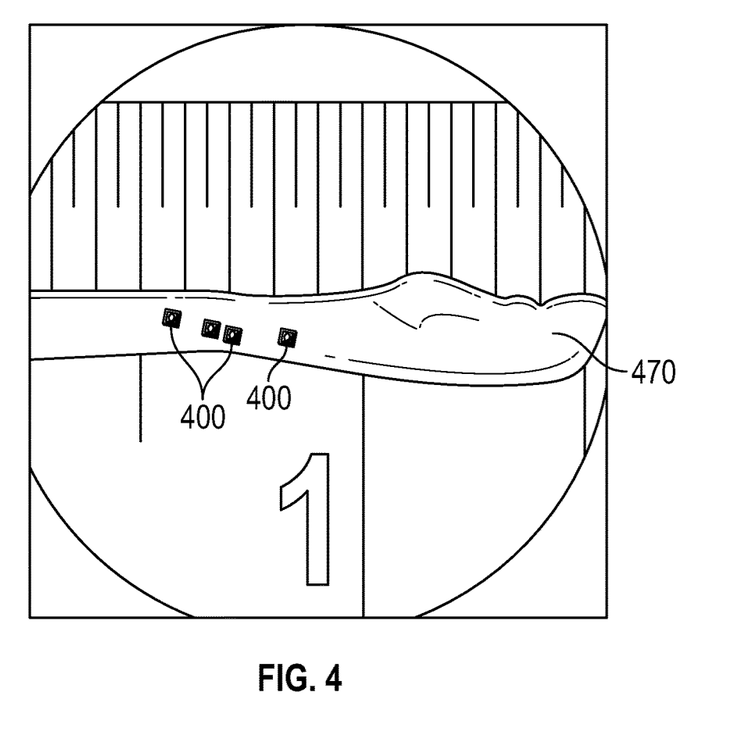
FIG. 4 shows four implantable micro-devices, proximate to a sciatic nerve in the foreground, as may be employed in certain embodiments.
Figure 5:
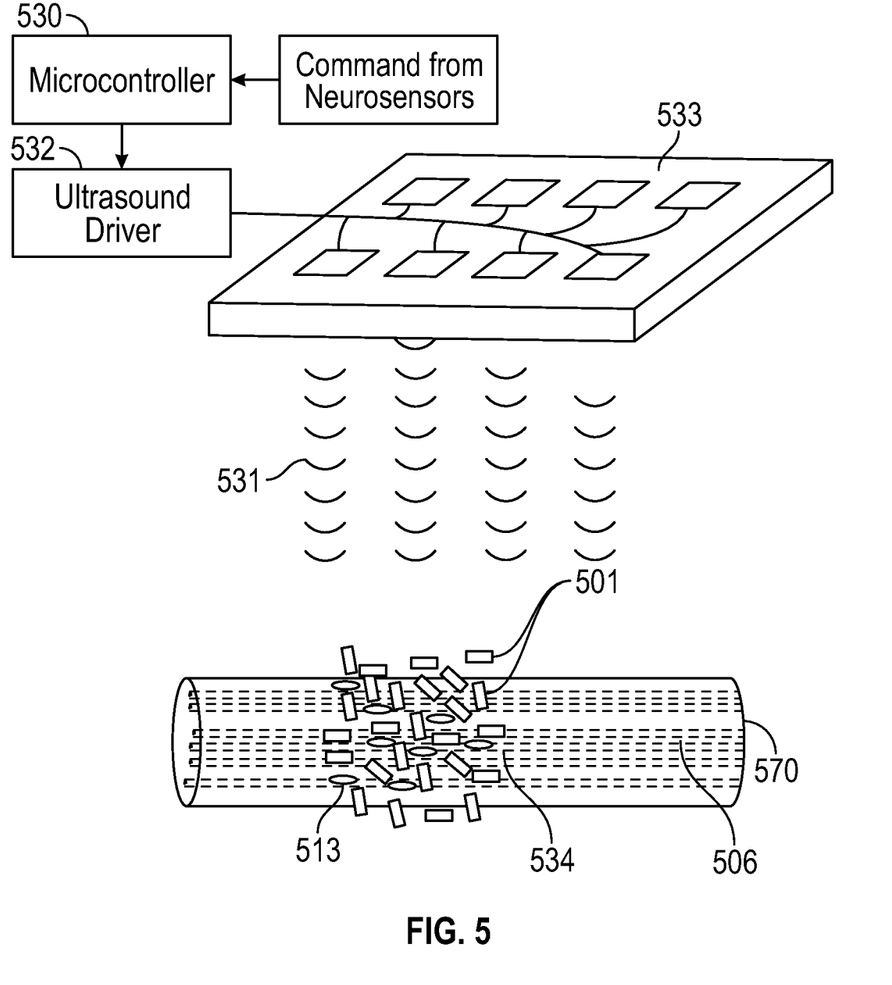
FIG. 5 shows a system with remote ultrasound emitters in communication with a piezoelectric slurry of micro-devices around a nerve and diodes inside the nerve, as may be employed in certain embodiments.

Embodiments may comprise a method of providing single and/or multichannel neurostimulation via implanted micro-devices, such as microminiature implanted diode devices. Exemplary microminiature diode devices can be implanted as seen in FIG. 4 and FIG. 5. In so doing, wireless transfer of power to the interior of nerve and other excitable tissues, for purposes of neurostimulation, can be provided. Additionally, neurostimulation may be scaled up via an increase in the numbers: of stimulation channels, of micro-devices, of groupings of micro-devices; and in other ways as well. Therapeutic effects of embodiments may promote healing, growth, regeneration, improved functionality of the targeted tissues, reduced cancer growth, or other beneficial effect.

Embodiments may employ slurries of micro-devices implanted in and around nerves wherein the micro-devices may be addressable by focused ultrasound waves. These ultrasound waves may be used to first locate implanted micro-devices and then later to provide tailored impulses that can be used to individually activate micro-devices or groupings of micro-devices. This activation may result in granular nerve fiber control or feedback for interfacing to or from a targeted nerve fiber or grouping of nerve fibers.

Details associated with the embodiments are described above and others are described below. Various modifications may be performed on the disclosed embodiments while remaining consistent with the scope of the disclosure. For example, devices, systems, processes, and articles of manufacture described herein may be configured as shown, may be modified such that they share features described elsewhere in this description, may be modified with fewer features than those described herein, and may also comprise other features not explicitly identified herein but nonetheless consistent with the teachings or disclosures provided in this application. Accordingly, the feature or features of one embodiment may be applied to other embodiments, even though not described or illustrated, unless expressly prohibited by this disclosure or the nature of the embodiments. Thus, there are various adaptations of embodiments, and many permutations, that may be employed within the spirit and scope of this disclosure. Those of skill will understand that the invention is not to be limited to only embodiments described herein and that other embodiments and applications consistent with the teachings herein would also fall with the scope of this disclosure.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Multichannel neural stimulation, which may have broad application to nerve, brain and excitable muscle tissue, is described and may be employed in various ways including generation of implantable bioelectrical stimulators for medical rehabilitation, replacement of lost function, and therapeutics. Affirmative and receptive neurostimulation may be provided or used in embodiments. Embodiments may also comprise methods, devices, systems, and articles of manufacture related to multichannel affirmative and/or receptive neurostimulation using implantable micro-devices. These micro-devices may be implanted in various patients, including humans, and may serve to send or receive neurostimulation signals to or from a target patient or group of patients. The level of granularity of the neurostimulation signals may provide for succinct or specific nerve control or nerve feedback. This specific nerve control or nerve feedback may be employed in various operations and apparatus, which can include control or monitoring of prosthetics, control or monitoring of implants, and treatment of diseased tissue or other target areas of a patient or group of patients. Proportional control as well as bipolar control and monitoring may also be provided in embodiments. In other words, embodiments may comprise methods, devices, systems, and articles of manufacture related to multichannel affirmative and/or receptive neurostimulation using implantable micro-devices where the affirmative and/or receptive neurostimulation may be performed or received on a proportional basis, i.e., in a range, or as high-low signal, i.e., having on and off or yes and no signal measurements—like a digital binary signal. Noise cancellation and smoothing techniques may also be employed in embodiments such that either or both proportional and binary neurostimulations may be employed. Thus, when a range or responses are received or signal noise is introduced when instructions are being sent, the noise cancelling and/or smoothing techniques may be employed to improve results.

Embodiments may be configured such that nerve fibers or subsets of nerve fibers or other nerve groupings of a nerve trunk may be uniquely stimulated or observed. This stimulation or observation, i.e., affirmative neurostimulation or receptive neurostimulation, may be employed on subsets of nerve trunks as well as individual nerve fibers. Micro-devices implanted in or proximate to nerves may serve as activating devices and/or receptors to communicate to and/or from specific nerve fibers, bundles of nerve fibers, or subsets of nerve trunks. Signals, such as ultrasound, may be employed to communicate to and from these implanted micro-devices. The signals may be tailored such that specific micro-devices are instructed or otherwise communicated with. These signals may be sent on an individual basis as well as in groups, such as in complex ultrasound wave fronts. The specific communications may allow for tailored instructions or feedback in certain embodiments. For example, a prosthetic may be controlled, in full or in part, by signals to and from micro-devices associated with one or more nerve fibers. This level of granularity can provide for improved control and/or feedback of a patient's prosthetic. The signals may comprise ultrasound waves and may be received by piezoelectric elements of a micro-device associated with one or more nerve fibers. The signals may be focused such that specific micro-devices are instructed by them. Likewise, micro-devices may send signals to be received by a microcontroller that can be attributable to a specific micro-device or grouping of micro-devices whereby specific feedback may be provided. The signals may also be sent as complex wave fronts to a micro-device or grouping of micro-devices. In embodiments, the micro-devices may be individually addressable as well as addressable as groupings and as a whole. In so doing, control and feedback to and from micro-devices may be provided across different levels of granularity of the micro-devices. These multi-channel communications, to and from individual or groupings of micro-devices, may provide for advanced neuro-prosthetic interfaces of nerves resulting in improved dexterity and improved man-machine interfaces. In certain embodiments, ultrasound frequency of activation signals intended for piezoelectric micro-devices may be increased into ranges of 250 kHz-50 MHz such that reduced sizes of micro-devices, on the order of magnitude of 0.05 mm to 3 mm, may be scanned for and controlled in embodiments. In general, the higher frequencies are employed with the smaller device scales.

Embodiments may provide an ability to activate the nervous system of a patient in specific ways via the use of a plurality of micro-devices incorporating semiconductor diodes implanted within bioelectrically excitable tissue that rectify externally applied volume currents. Implanted diodes, in embodiments, may produce neurostimulation by way of a staged energy transfer process where ultrasound is directed to piezoelectric ceramics, located external to excited tissue and are the source of volume currents. Embodiment may also comprise wired electrodes driven by a multichannel pulse generator placed in proximity and external to tissue, which are the source of volume currents.

Embodiments may employ micro-devices that are interspersed and not necessarily having wired connections where ultra-sound microbeams may be directed to one or more micro-devices in order to convert that micro-beam into a neurostimulation of a nerve fiber or group of nerve fibers. The ultrasound beams may be highly focusable—created by an array and focused via a lens. Through targeted microbeams, different parts of a nerve may be stimulated via the implanted micro-devices. Moreover, multiple channels may be created via individual or groupings of micro-devices and in so doing voluntary control of prosthetics may be performed. Likewise, feedback may also be provided from the micro-devices, further aiding the control of prosthetics.

In embodiments, a short pulse of alternating current broadly dispersed through tissue from remote non-contacting electrodes can be rectified locally by a micro-device such as a diode that is sufficiently small as to be placed within a nerve where it only contacts a single nerve fascicle out of many. Many such diodes or other micro-devices having sizes on the order of 100 micrometers and smaller can be distributed within a nerve and when actuated by an external high frequency current passing through tissue will create neurostimulation local to diode placement. Accordingly, embodiments may provide complex high frequency electric field distributions around and within a nerve involving strong electric field gradients. Diodes or other micro-devices may be employed to rectify only dipolar fields having a gradient across their length where they contact tissue. In so doing, there is a complex electric field generated by a multiplicity of remote sources which may be used in embodiments, through varying combinations of fields, to be selective as to which diodes are actuated. In embodiments, through complex electric field gradients, subsets of diodes or even single diodes, or other micro-devices may be actuated, thus allowing multichannel neurostimulation.

It is preferred in embodiments that electrical sources needed to create volume currents be preferably placed in external proximity to the nerve but not necessarily touching the nerve. In such embodiments, an electrical stimulation device, such as a diode or other micro-device, is free floating within the nerve. There are preferably no wires connecting to it. Absent connecting wires, there is no possibility that wires will create damage through their movement. Thus, in certain embodiments complex but yet controllable external fields that thread in and around the nerve may be created by use of ultrasound driving the emission of electric fields from implanted piezoelectric materials in proximity to a nerve. The piezoelectrics can serve to convert ultrasound energy to multiple discrete electrical signals at many locations through electronic sweeping of the ultrasound beam and locally activate parts of the nerve. By these methods there can be achieved multichannel functionality without wired connection to the interior of the nerve.

With regard to treatment, micro-device embodiments may be used in place of drug therapeutics as well as in conjunction with drug therapeutics. Embodiments may differ from only drug therapies in the sense that administered oral medications or other drug therapeutics may undesirably circulate throughout the entire body of a patient, creating side effects, while neurostimulator embodiments may focus on a precise area or pain sensation. Accordingly, drug therapies may not be preferred or as efficient as tailored neurostimulator treatments that may be performed consistent with certain embodiments.

As to prosthetics, neurostimulation embodiments may be employed in the design of advanced medical prosthetics that are controlled through interface with the nervous system of an amputee. In these prosthetics, wireless neurostimulator micro-devices may be placed on or proximate to a nerve surface and held in place by a silicone cuff. Embodiments may also employ implantable micro-devices, such as micro-neurostimulators. Micro-devices in these and other embodiments may employ communication technologies comprising induction coil, microwave dipole, photodiode, or piezoelectric materials. These communication technologies, which have varying efficiencies and practicalities, absorb incoming energy from external drivers and convert the incoming energy to electrical stimulus pulses needed for the nerve. The implantable micro-devices are preferred at least to the extent that they may serve to reduce mechanical trauma to the nerve during placement, stretching from electrode leads that pull on the nerve cuff during motion, and injuries from a long-term electrode pressure on the nerve, which may each be experienced when wireless neurostimulators are be placed on or proximate to a nerve surface and held in place by a silicone cuff or other attachment system.

As to the control signals to and from the micro-devices, and as identified above, embodiments may employ ultrasonic transcutaneous energy transfer (UTES), which may have notable advantages over other communication technologies identified above. For example, magnetic induction may not be preferred in embodiments as magnetic induction may suffer from relatively large coil size requirements, poor power coupling to small sized implants, and high eddy current loss in the underlying skin during its operation. The efficiency of the ultrasound powered neurostimulation method using UTES may rely on accurate focusing of ultrasound signals to an implant for maximum energy transfer and for specific addressing of a signal to a desired micro-device.

Thus, embodiments may provide systems and/or processes whereby an implantable neurostimulator can be realized in a multichannel configuration. Embodiments may also provide systems and/or processes whereby nerves can be implanted with microscale diode rectifier micro-devices which, when in the presence of volume conducted currents, can affect fascicular-level stimulation within a nerve. In so doing, embodiments may provide tailored specific and powerful control over body functions. In certain embodiments, systems and/or processes may provide an ultrasound means to generate the required complexity of volume currents surrounding a nerve through its beam direction in sequence or in parallel to multiple implanted piezoelectric ceramics. Also, systems and/or processes of embodiments may provide complex volume driven currents sufficient to drive implanted diodes or other micro-devices by way of tissue electrodes driving high frequency AC currents.

Certain embodiments may provide high density neurostimulation of the CNS using wireless piezoelectrically powered implanted microdevices actuated by remote ultrasound beams. Piezoelectric ceramic chips on the order of less than 100 microns may be employed to produce tens to hundreds of millivolts with the application of a scanning focused ultrasound beam of the type used in medical imaging. When ultrasound energy is rectified by an on-chip diode of similarly small size, the microchip may produce electric current pulses within the range of cortical neurostimulation.

In so doing, on the millimeter-order size scale, embodiments may serve to stimulate peripheral nerves with milliampere-order generated currents.

In embodiments, large numbers (1000's or more) of microscale passive devices may be dispersed on the brain cortical surface, within the brain itself, or elsewhere. This deployment may be performed using conformal sheets, injection, blood transport, stents, etc. Neurostimulation may be performed on a robust scale in embodiments by using externally positioned and compact ultrasound beam forming technologies that electronically position beams that can serially scan 512×512 matrices of tissue in 30 ms. These scanning systems may serve to actuate 105 or larger numbers of micro-devices. Embodiments may apply ultrasound power levels focused to submillimeter spot sizes on the order of 750 mW/cm2. In embodiments, the needs of neurostimulation of cortical tissue of the CNS can requires less than a microwatt. As such, acoustic losses on the order of 105 can be tolerated along the beam penetration path. Scanning may be employed in embodiments to locate implanted micro-devices and map their location for subsequent neurostimulation and control. This mapping and subsequent stimulation may be performed by the same controller as well as by different processors that are adapted to share or otherwise use the same data related to the location of the implanted micro-devices.

Figure 1:
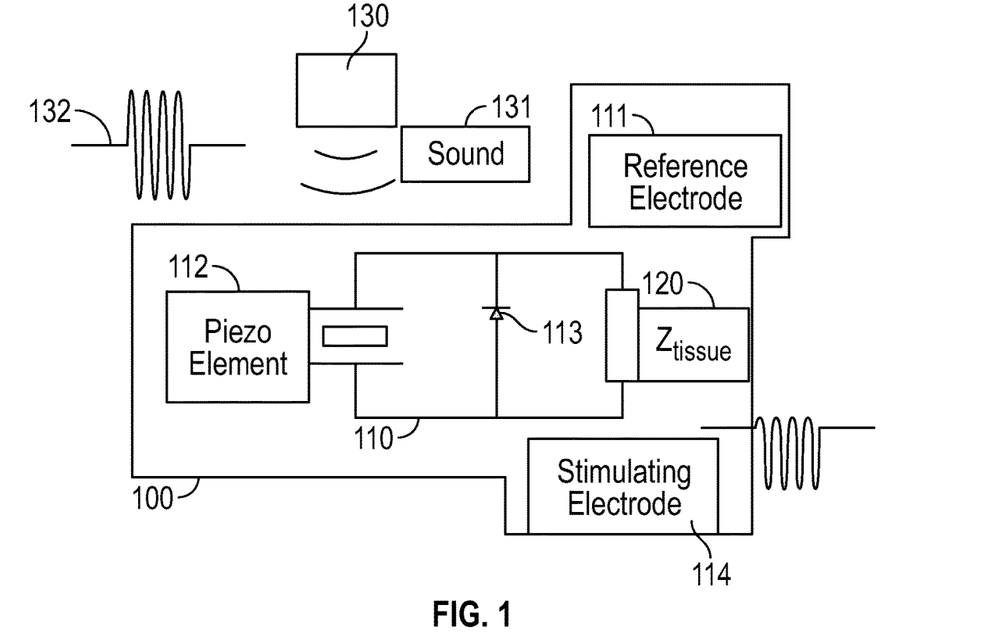
FIG. 1 shows an electrical circuit of an implant with the circuit terminated in a tissue load as may be employed in certain embodiments.
Figure 3A:
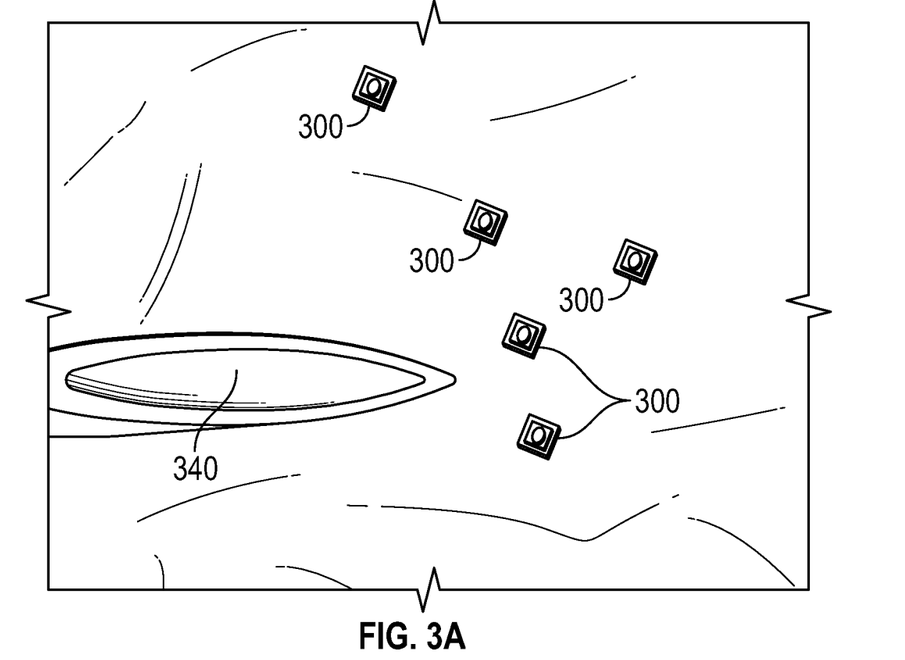
FIGS. 3A-3C show implantable micro-devices as may be employed in certain embodiments.
Figure 3B:
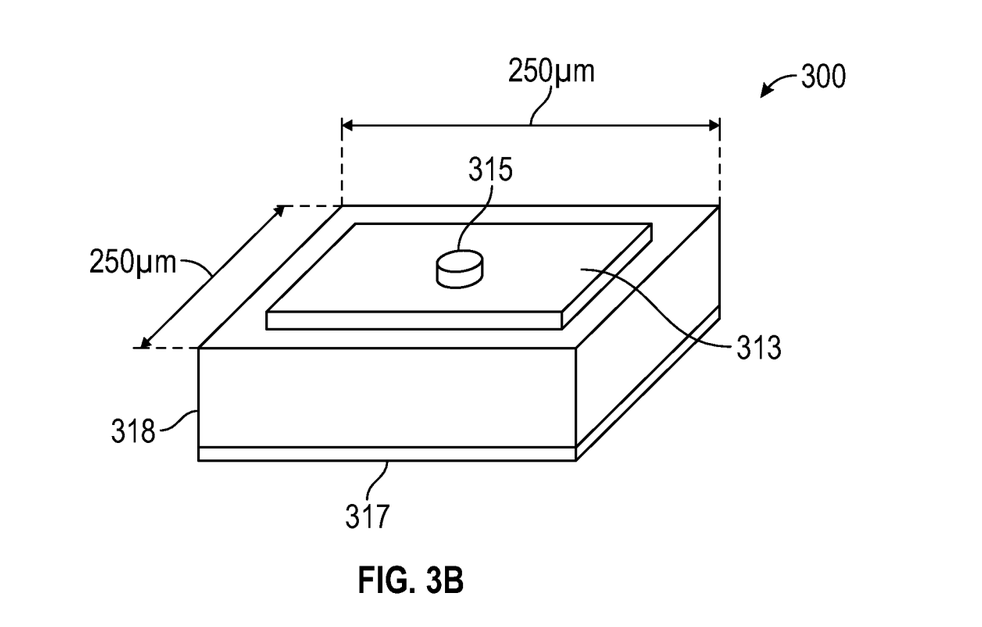
Figure 3C:
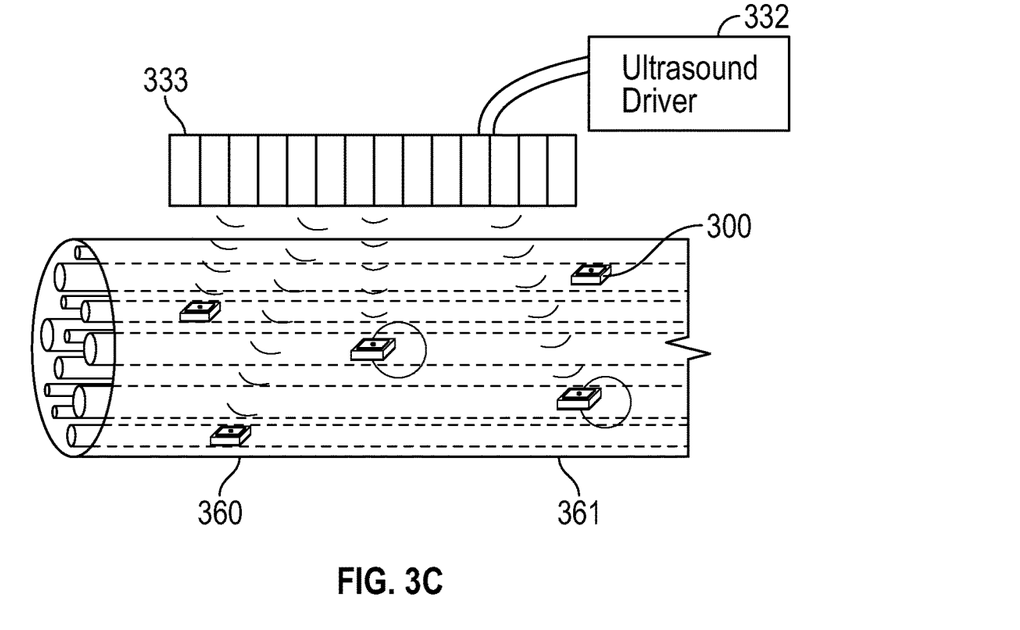

FIG. 1 shows an electrical circuit 110 of an implant 100 with the circuit 110 terminated in a tissue load 120 as may be employed in certain embodiments. Also labelled in FIG. 1 are a reference electrode 111 of circuit 110, a piezoelement of circuit 110, a diode 113 of circuit 110, a stimulating electrode 114 of circuit 110, a sound emitting controller 130, sound waves 131 from the controller 130, and an input signal 132 for the controller 130. In embodiments, like those of FIG. 1, a small implantable diode device (typically on the order of 100 microns diameter and less), which is preferably small enough to be permanently placed within or in proximity to a nerve, is used to provide localized rectification of AC volume currents sufficient to cause neurostimulation. The implant 100 is small enough such that it may be introduced into a nerve through a hollow syringe-type introducer, as can be seen in FIG. 3. The suitability of neurostimulation implants, such as the implant 100 of FIG. 1, for medical application may be preferably particularly enhanced through the use of thin ceramic packaging for the implant. Ceramic packaging encapsulation is possible because ultrasound energy will pass, although with some loss, through thin ceramics such as alumina and zirconia appropriate for their high strength and excellent biocompatibility.

Figure 2:
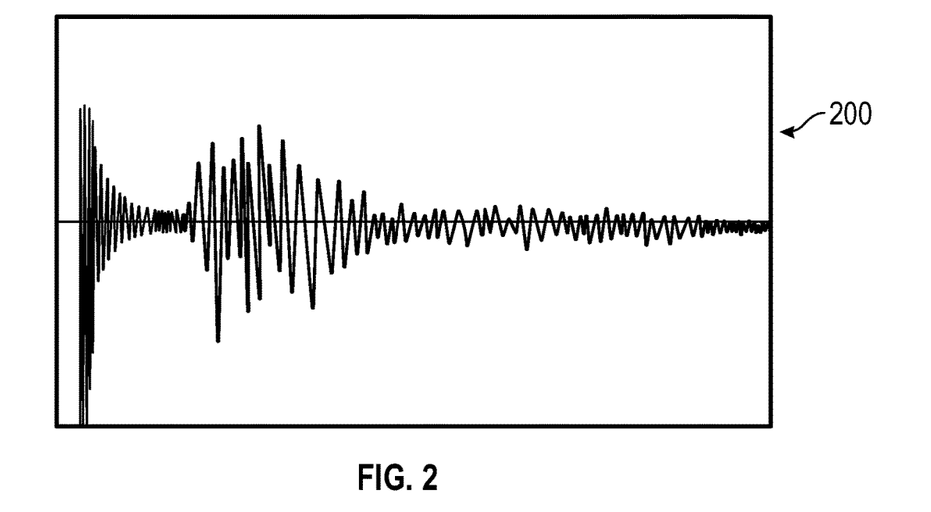
FIG. 2 shows an electrical signal detected from a piezoelectric PZT-5A slurry using microelectrode micro-devices as may be employed in certain embodiments.
Figure 6:
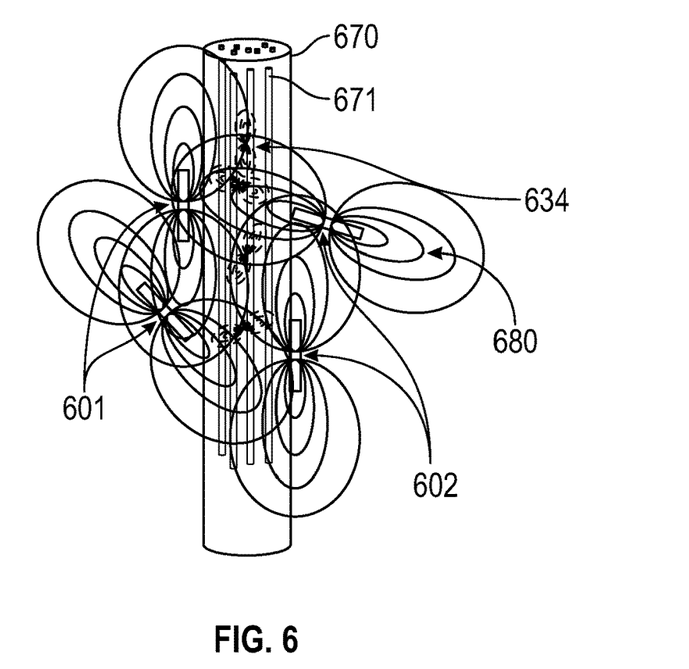
FIG. 6 shows piezoelectric element micro-devices in random orientations surrounding a nerve producing ultrasound driven electric fields that extend into the nerve and are locally rectified by diodes at fascicules, as may be employed in certain embodiments.

As can be seen in FIG. 1, embodiments may employ a high frequency current that is generated by an implanted piezoelectric material during an ultrasound stimulus. The piezoelectric material 112 consists of a plurality of typically millimeter-order solid state crystalline materials arranged as an ordered array or slurry of random particles external to the nerve, as can be seen in FIGS. 2 and 6. These create a source-sink current flow upon ultrasound application from a remote transducer. A number of independent channels can be achieved by this approach and may be scaled up. A limiting factor on the number of independent channels can be the size and density of diodes introduced within the nerve bundle. The diodes, however, can be distributed not only transversely in the nerve but axially down the length of the nerve. The number of possible channels may be dependent on the number of unique ultrasound beam combinations, and this would be expected to be in a factorial relationship to their numbers in certain embodiments.

Embodiments may rely on a recognition that high frequency alternating currents can be passed through biological tissue at relatively high non-thermal current levels, but produce no observable effects on bioelectrically excitable tissues. However, if such currents are locally rectified by a free-floating diode or other micro-device in tissue, the resulting monophasic currents can be locally stimulatory to nearby excitable tissue. More specifically, nerves are insensitive to tens of kilohertz to megahertz-range high frequency alternating electric currents (AC) and cannot be stimulated by them to an action event. The physiologic reason for this is considered to be that high frequency waveforms are far faster than the natural time course of membrane bioelectric events. AC current driven depolarization then repolarization of cell membranes occurs so fast that ion channel kinetics cannot follow. Similarly, fast but monophasic currents are apparently integrated by nerve cell membranes to direct current, and so create a net effect. Thus, embodiments can provide configurations or processes whereby a nerve responds to the pulse envelop of the AC current pulse and not its frequency. These configurations and processes may be employed using the implant 100 of FIG. 1 as well as other configurations of micro-devices. Miniature semiconductor diodes may be employed in embodiments to rectify local volume AC currents in tissues and transform them to a pulsating DC current, which embodiments may employ in neurostimulatory applications. In so doing, embodiments may provide wireless neurostimulation into a nerve bundle and an ability to actuate a plurality of independent channels.

Micro-devices of embodiments may comprise integral electrodes at either end of a cylindrical length. The micro-devices may also comprise diode rectifiers 113 made of a semiconductive material, as shown in FIG. 1, which may perform the function of producing a pulsating DC from a high frequency AC current present across an output electrode 114. Thus, embodiments may comprise a millimeter-order piezoelectric chip mated to a small diode when placed near a nerve in order to evoke action events when illuminated by a remote source of ultrasound energy. Both peripheral as well as central nervous systems may be targeted in embodiments.

FIG. 2 shows the electrical signal 200 detected from a piezoelectric PZT-5A slurry using microelectrodes placed 2 mm apart using ultrasound at 2.5 MHz, 30 mW/cm2. (scale 10 mV/div, 5 us/div) as may be employed in embodiments. A saline slurry of 100 piezoelectric chips diced from 100 micron thin sheets of gold-electroded PZT-5A into 100 micron squares in combination with 30 Schottky die diodes 200 micron square were dispersed in a small 1 cc fluid delay column with a 2.5 MHz ultrasound transducer applied from various directions. Ultrasound neurostimulation can be visualized on the imaging display of an ultrasound machine by the method taught in PCT/US04/16417 (Towe) "Piezo Micro-Markers for Ultrasound Medical Diagnostics," which is hereby incorporated by reference in its entirety.

Polyimide insulated tungsten microelectrodes insulated to their exposed tip (FHC Corp, 1201 Main Street, Bowdoin, Me., USA 04287) held about 1-2 mm apart may be randomly inserted into the slurry in embodiments. A pulse approach may be preferred to insure against drive burst artifacts. The randomness of the dispersed piezoelectric powders in their orientation and position may serve to provide that at a given distribution organization there are some that are aligned to both the ultrasound beam and the detection electrodes.

FIG. 3A shows a photomicrograph of assembled, approximately 250 μm square PZT/Schottky diode, micro-device implants 300 compared to a 16-gauge syringe needle point shown for reference (coming from the left). FIG. 3B shows a micro-device implant 300 with cathode 315, diode 313, anode (palladium) 317 and piezoelectric polymer 318. FIG. 3C shows proposed micro-device implant neurostimulator slurry of five micro-device implants 300 positioned around an intra-epineurial nerve. As shown in FIG. 3C, in embodiments, a nerve may receive a slurry of micro-devices as a bolus and these micro-devices may be somewhat uniformly located about the nerve or other target area. The micro-devices may be contained in cylindrical casing to facilitate injection but other casing shapes may also be used. The sizes of the micro-devices may vary and may include casing sizes having dimensions in the range of 10 microns to 100 microns in thickness and preferably on the order of 0.01 to 1 mm length. The micro-devices may consist of only piezoelectrics or diodes as shown in FIG. 5.

As shown in FIG. 3C, embodiments may comprise a plurality of piezoelectric devices placed in proximity to a nerve. During operation, these micro-devices may be driven by pulsed ultrasound energy individually or in multiples, whereby they convert acoustic energy to high frequency AC currents in tissue. These currents propagate according to rules of electric field conduction through tissue and nerve so to cause electric field gradients of complex distribution because of the multiplicity of beams and piezoelectric generators. It is the ability of electrical currents to pass through the epineuria and outer fat sheathing of the nerve and then be intercepted by internal free-floating microelectronic devices that produce bioelectrical effects that is of significant advantage of this invention. Preferably, there is no penetration of the nerve by connecting wires and thus natural motion of the nerve with body movement does not drag or tug on them. There are, rather, one or more electronic devices which are coupled through electric fields.

In embodiments, neurostimulation currents produced locally by an implanted diode, for example, which may be prescribed by a physician, may preferably be in the range of 50-microampere range and often less to achieve stimulation. A sufficiency of ultrasound power can be relatively moderate, typically in the range of 10 mW/cm2 to several 100's mW/cm2 Isptp., and preferably substantially below FDA limits in the United States of 720 mW/cm2.

The ultrasound frequency in such applications may be selected from a range typically within that of 100 kHz to 50 MHz, but preferably in the range of 750 kHz to 7.50 MHz. Tradeoffs in the selection of the operating frequency include a greater tissue penetration and lower loss at low frequencies. However, the beam focal spot can be smaller at higher frequencies thus allowing greater numbers of channels, more specific addressing of individual micro-devices, better granularity for mapping micro-deices, but poorer penetration depths. The selected frequency can preferably depend on the specific application.

In certain embodiments, a plurality of diodes may be integrated together into the surface of a thin biodegradable substrate as an array whereby they have a common bioelectrical contact at one end of the substrate. The uncommon diode contacts may be routed to very fine thin film insulated conductors which extend over the surface of the substrate length, which may be a length of several hundreds of microns to millimeters. Ultrasound drivers that may be employed in embodiments may include 2 cm diameter focused transducers with approximately 100 micron focal spots driven to approximately 50 mW/cm2 power levels that are with the FDA safe limits SPTA 720 mW/cm2 or 180 W/cm2 SPTP for use on adults.

An exemplary relative size of a target nerve and implantable micro-devices in embodiments is shown in FIG. 4. Four experimental piezoelectric stimulators 0.25 mm square "neuro-chips" 400 on an excised rat sciatic nerve 470 being evaluated for the potential to stimulate fasicularly, where lower currents are acceptable, are labelled in FIG. 4.

FIG. 5 shows an illustration of micro-device piezoelectric slurry 501 around a nerve 570, micro-device diodes 513 inside the nerve 570, and remote ultrasound emitters 533. Also labelled are microcontroller 530, ultrasound driver 532, ultrasound beams 531, and complex electric fields 534.

Figure 7:
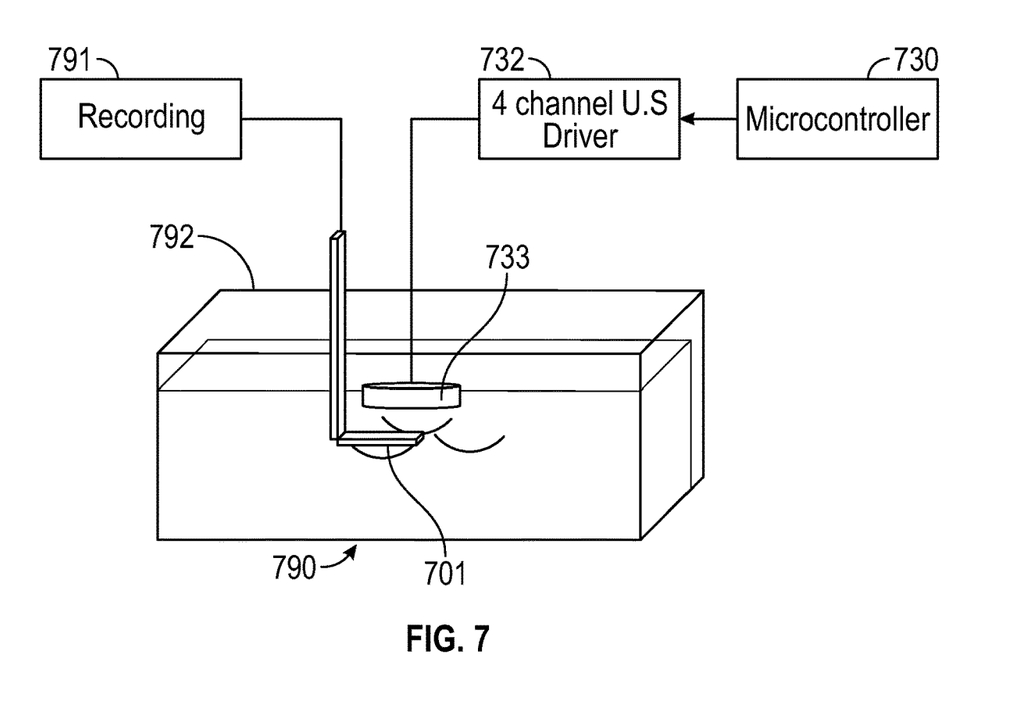
FIG. 7 shows a micro-device test tank system as may be employed in certain embodiments.
Figure 8:
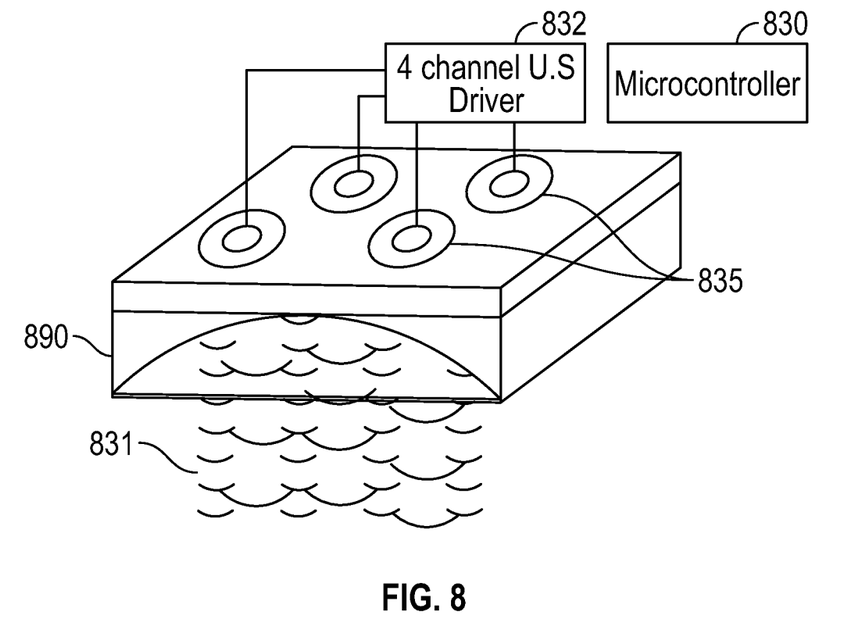
FIG. 8 shows a multi-channel ultrasound emitter as may be employed in certain embodiments.

In FIG. 5, as well as other embodiments, a microcontroller 530 software program may be programmed to actuate a single or multiple ultrasound emitter 533 directed at the micro-device piezo-materials near the implants, as seen in FIGS. 5, 7, and 8. The ultrasound emitter 533 is preferably thin, planar, and compact and placed on the body surface over the implants. The body surface unit may employ surface bioelectrodes to monitor an electrical signal originating from the electrical activity of the implant according to Towe (U.S. patent publication 20170095198), hereby incorporated by reference. This configuration can be seen in FIG. 5. From the amplitude of the ultrasound-evoked returned signal the microcontroller may be configured to determine which one or combination of piezoelectric emitters of the micro-devices are actuated and so provides a feedback signal to adjust for variation in position of the ultrasound emitters of the micro-devices. The micro-devices and systems employing them may employ passive RFID communication techniques. For example, the micro-devices may contain passive antennas that reflect different frequencies back when activated. These unique reflections may be employed to identify and signal individual micro-devices of the slurry 501.

Piezoelectric particle sizes described herein may be too large as a slurry to introduce into the body of a nerve axon but suitable for surrounding a nerve. When introduced as a slurry, the generated electric fields will crisscross the nerve body if the slurry surrounds it. In some embodiments, the use of a neurostimulation slurry may employ dual placements whereby the diodes are placed within the nerve body where they locally rectify MHz currents in the nerve to cause stimulation of fascicles and epineurial placement of the piezoelectric particles that are actuated by ultrasound. The combination of these two seeks to provide minimal trauma within the nerve. The diodes recruit power from the piezoelectric elements and at the focus of ultrasound converts its signal envelope into a stimulation pulse. Thus, essentially any amplitude or wave shape of the stimulation pulse can be created since its defined by the software-controlled pulse characteristics of an externally worn ultrasound generator.

As to power, the energy demands of neurostimulation on a pulse-pulse basis are miniscule, amounting to microwatts, while focal ultrasound at pulse power densities at 190 W/cm2 are permissible by FDA standards. Accordingly, there may be a permissible loss of more than 105 in certain embodiments.

FIG. 6 shows an illustration of piezoelectric elements 601 and 602 surrounding a nerve 670 producing ultrasound driven electric fields 680 that extend into the nerve and are locally rectified by diodes at fascicules. As can be seen, the electric fields are orientated with the casing of the micro-devices. Also labelled in FIG. 6 are the nerve fibrils 671, complex distributed field lines 680, and miniature diodes 634 inside the nerve bundle 670. In one embodiment, a random orientation and positioning of ultraminiature diodes can be employed for their easier introduction to nerve via a fluid carrier. Their random positioning is one method to maximize the number of independent stimulation channels. This is because diode rectification of ac currents occurs by a dot product relationship. Local nerve fiber threshold is only achieved when the summed piezoelectric currents are aligned so that the dot product of the specific diode vector direction are aligned. Thus, single or combinations of ultrasound beams from different directions and directed towards the ensemble of piezoelectrics will activate unique combinations of diodes. The single or combinations of nerve activations can be determined by observing physiologic function changes and then entering the observed results into a computer based mapping program that then can actuate specific physiologic function upon command.

Likewise, although less desirably and with less specificity of effect, a multiplicity of remote ac current driving electrodes can be employed rather then piezoelectric elements. In this case, electrodes are disposed to provide a multiplicity of selectable current vectors that allow for activation of nerve fibers, or combinations of nerve fibers, where the dot product of the diode orientation and the currents are maximized and so meet required nerve thresholds.

In certain embodiments, the complexity of electric fields induced inside the nerve by local sources on the nerve body in combination with a relatively high density of dispersed detector diodes within, can be responsible for the potentially large number of independent points of neurostimulation. In embodiments, there may not be a need to know exactly where the stimulation points occur rather just an attempt to achieve many independent ones that can be varied as the vector, time course, and power levels of a complex beam of ultrasound is directed towards the nerve. The changes in the ultrasound energy directed at the piezoelectrics from potentially multiple closely spaced transducers having different delays, phases, amplitudes creating a complexity of wave fronts and possibly vector directions that can provide the potential for a large number of potential stimulation points in embodiments.

The slurry approach in embodiments may depend on the decoupling of the energy transducer function of the piezoelectrics from the rectification function of the diodes. This may allow the piezoelectric ceramic chips to be relatively larger and thicker, for example a 100 microns cube, which may serve to increase their ultrasound capture efficiency compared to the few tens of microns in size that would be less traumatic to implant within the nerve. This decoupling of the piezoelectric from the diode is less efficient compared to the situation where diode is placed directly against a piezoelectric. It however allows the diode portion of the pair to be relatively smaller and much thinner, perhaps on the order of a few micrometers.

FIG. 7 shows an illustration of a test tank configuration. Some embodiments of the invention can be tested as shown in the configuration of FIG. 7. Labelled in FIG. 7 are the recording device 791, a 4-channel U.S. driver 732, a microcontroller 730, a manipulator 792, an emitter array 733, a tank 790 with saline, and a piezoelectric slurry 701. When testing embodiments, micro-device piezoelectric elements and micro-device diodes may be arranged in a saline test tank in a way similar to how they would be placed around a nerve by a carrier liquid. Both random placement orientations as well as ordered arrangements in various strategies may be explored in the testing tank.

FIG. 8 shows an illustration of a multiple channel ultrasound emitter with piezolelectric emitter pads 835, acoustic lens 890, 4 channel ultrasound driver 832, and microcontroller 830. As can be seen, a complex ultrasound wave front 831 may be created by the pads 835 and subsequently focused by the lens 890.

Figure 9:
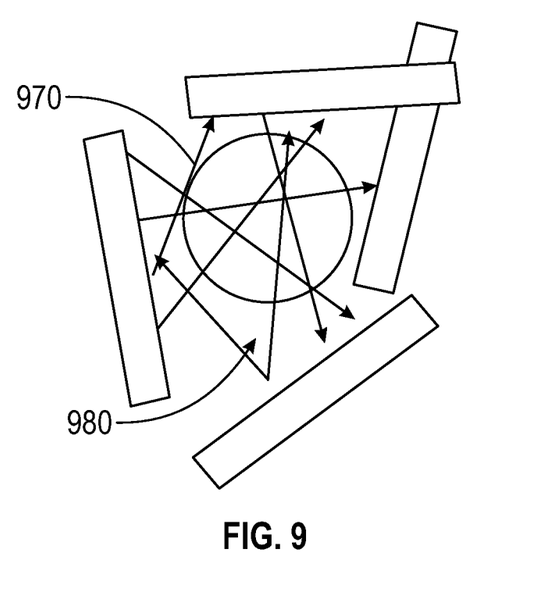
FIG. 9 shows a nerve bundle crisscrossed by complex electric fields produced by micro-devices as may be employed in certain embodiments.

FIG. 9 shows a nerve bundle 970 surrounded by a slurry of micro-devices that are acting to create complex electrical fields 980 through the nerve. The view of FIG. 9 is a cross-sectional view as compared to FIG. 6, which shows a partial side-view. As shown in FIG. 9, each piezoelectric element may create an electric field. When used in conjunction with micro-devices, a complex distributed electric field may be created around and within the nerve that is locally rectified by the diode slurry. In embodiments, the piezoelectrics may be sensitive to ultrasound frequency, acoustic field distribution, and particularly to phase relationships if interacting with multiple ultrasound waves. Body surface ultrasound transducers positioned in an array can be directed to excite the piezoelectric slurry of FIG. 9. Other activation designs may also be used. When calibrating the transducers, a design criterion can be frequency, where higher frequencies are considered to be more efficient but less penetrating. The needed penetration depth of the ultrasound to a specific nerve may be a prevalent determining factor and this would likely vary between specific applications. In preferred embodiments, piezoelectric elements should be of thickness not much smaller than the acoustic half-wavelength, At nerve locations within five centimeters of the skin, like the radial nerve in the arm, the frequency may preferably be less than about 2.5 MHz depending on the design criteria. This can result in the size of the piezoelectric elements in the slurry to be relatively large, about 300 microns in thickness and square dimension. When relatively large sizes are employed, the piezoelectric elements may preferably reside outside of the nerve axon. The diodes, which have a smaller dimension however could be infused into the nerve to provide local rectifications. Larger path lengths would scale as a function of decreasing frequency. Shorter path lengths such as the vagus at 2 cm deep may preferably use 5-10 MHz with piezoelectric chips of size on the order of 75-150 micrometers. Encapsulation of the micro-devices may comprise NIPAM, parylene or other well-known vapor deposited materials, sputtered or applied by other methods known in the semiconductor packaging may be required to enhance biocompatibility.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" and/or "comprising," when used in this specification, specific the presence of stated features, integers, steps, operations, elements, and/or components, but do not preclude the presence or addition of one or more other features, integers, steps, operation, elements, components, and/or groups thereof.

It should be noted that terms "first", "second", and "third", and the like may be used herein to modify elements performing similar and/or analogous functions. These modifiers do not imply a spatial, sequential, or hierarchical order to the modified elements unless specifically stated.

As used herein, the terms "about" or "approximately" in reference to a recited numeric value, including for example, whole numbers, fractions, and/or percentages, generally indicates that the recited numeric value encompasses a range of numerical values (e.g., +/−5% to 10% of the recited value) that one of ordinary skill in the art would consider equivalent to the recited value (e.g., performing substantially the same function, acting in substantially the same way, and/or having substantially the same result). As used herein, the terms "about" or "approximately" in reference to a recited characteristic, generally indicates that the recited characteristic encompasses a range of variations on the characteristic that one of ordinary skill in the art would consider equivalent to the recited characteristic (e.g., performing substantially the same function, acting in substantially the same way, and/or having substantially the same result).

Recitation of ranges of values herein are merely intended to serve as a shorthand method of referring individually to each separate value falling within the range, unless otherwise indicated herein, and each separate value is incorporated into the specification as if it were individually recited herein.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

The description of the embodiments of the present invention has been presented for purposes of illustration and description but is not intended to be exhaustive or limited to the invention in the form disclosed. Many modifications and variations will be apparent to those of ordinary skill without departing from the scope and spirit of the invention. The embodiments were chosen and described in order to best explain the principles of the invention and the practical application, and to enable others of ordinary skill in the art to understand the invention for embodiments with various modifications as are suited to the particular use contemplated.

What is claimed is:

1. A neurostimulator system, comprising:
   a first slurry of semiconductor diodes having biocompatible packaging and bioelectrodes on a surface of the packaging, the semiconductor diodes configured to rectify volume AC currents;
   a surgical introducer configured to implant the semiconductor diodes into bioelectrically excitable tissues;
   a second slurry of piezoelectric elements; and
   an ultrasound emitting transducer configured to be pulsed and focused to deliver wireless acoustic energy to the piezoelectric elements sufficient to cause the piezoelectric elements to produce volume AC currents around the piezoelectric elements that will stimulate at least one semiconductor diode.

2. The neurostimulator system of claim 1, wherein the biocompatible packaging comprises an encapsulant coating comprising PARALYENE and/or BIONATE.

3. The neurostimulator system of claim 1, wherein:
   the semiconductor diodes comprise at least two neurostimulator diodes; and
   the at least two neurostimulator diodes are electrically in series and/or parallel.

4. The neurostimulator system of claim 1, wherein the piezoelectric elements comprise a biocompatible ceramic polymer.

5. A method of neurostimulation using the neurostimulator system of claim 1, the method comprising:
   implanting the first slurry of semiconductor diodes within bioelectrically excitable tissue of a patient;
   implanting the second slurry of piezoelectric elements within two inches of the bioelectrically excitable tissue of the patient;
   applying wireless ultrasound energy from a location outside of the patient, wherein the ultrasound energy provides energy to generate simple or complex volume AC currents from one or more of the piezoelectric elements; and
   achieving rectification by one or more of the semiconductor diodes, the rectification serving to provide a bioelectrical stimulation event of the bioelectrically excitable tissue of the patient.

6. The method of claim 5, wherein the bioelectrically excitable tissue of the patient is nerve, muscle, or brain tissue.

7. The method of claim 5, wherein ultrasound pulses of the ultrasound energy have a duration in the range of 0.1 millisecond to 10 milliseconds, or a frequency of 1 to 1,000 pulses per second, or both the duration and the frequency.

8. The method of claim 5, wherein ultrasound pulses of the ultrasound energy are generated by a phased array, linear array, or sector scanner system.

9. The method of claim 5, wherein ultrasound pulses of the ultrasound energy are generated by a series of discrete emitter elements that are distributed in space from each other.

10. The method of claim 5, wherein ultrasound pulses of the ultrasound energy are generated by one or more ultrasound transducers placed on a body surface of the patient.

11. The method of claim 5, wherein the bioelectrodes are configured to be excited with DC or AC current pulses having amplitudes in the range of 0.01 milliampere to 5 milliamperes.

12. A method of neurostimulation using the neurostimulator system of claim 1, the method comprising:
   introducing the first slurry of semiconductor diodes, wherein:
     the semiconductor diodes are directly implanted within the bioelectrically excitable tissues, or
     the bioelectrodes of the semiconductor diodes are integrated and are in surface contact with the bioelectrically excitable tissues;
   placing one or more of the piezoelectric elements in proximity to the bioelectrically excitable tissues and the semiconductor diodes;
   applying wireless ultrasound energy to the one or more piezoelectric elements so as to create simple or complex volume AC currents that enclose a region of the semiconductor diodes; and achieving rectification by the semiconductor diodes and a resulting bioelectrical stimulation event of the bioelectrically excitable tissues.

13. The method of claim 12, wherein the bioelectrically excitable tissue is nerve, muscle, or brain tissue.

14. The method of claim 12, wherein the ultrasound is pulsed with parameters in the range of 0.1 millisecond to 10 milliseconds at a repetition rate of 1 to 100 pulses per second, causing a corresponding timed and amplitude response in an implanted current flow.

15. The method of claim 12, where the ultrasound is generated by an electronically steerable phased array, linear array, sector scanner, or harmonic imaging system.

16. The method of claim 12, where the ultrasound is generated by a series of discrete emitter elements which are distributed within or surrounding tissue such as to maximize their ability to stimulate a large number of the piezoelectric elements located on or near the bioelectrically excitable tissues.

17. The method of claim 12, wherein:

the semiconductor diodes comprise multiple neurostimulators:

the multiple neurostimulators are placed in electrical series and/or parallel; and the multiple neurostimulators are activated by one or more ultrasound transducers comprising the ultrasound emitting transducer and placed remotely.

18. The neurostimulator of claim 1, wherein the semiconductor diodes are individually addressable.

19. The neurostimulator of claim 1, wherein the piezoelectric elements are to be implanted around the bioelectrically excitable tissues.

20. The method of claim 5, wherein the piezoelectric elements are individually addressable.

* * * * *